United States Patent [19]
Radtke et al.

[11] Patent Number: 6,051,420
[45] Date of Patent: Apr. 18, 2000

[54] METHOD FOR THE DECONTAMINATION OF SOIL CONTAINING SOLID ORGANIC EXPLOSIVES THEREIN

[75] Inventors: Corey W. Radtke; Francisco F. Roberto, both of Idaho Falls, Id.

[73] Assignee: Bechtel BWXT Idaho, LLC, Idaho Falls, Id.

[21] Appl. No.: 09/082,421

[22] Filed: May 20, 1998

Related U.S. Application Data

[60] Provisional application No. 60/047,280, May 21, 1997.

[51] Int. Cl.⁷ .............................. C12S 13/00; B09B 3/00
[52] U.S. Cl. ...................... 435/262.5; 435/262; 588/202
[58] Field of Search .............................. 435/262.5, 262; 71/8–10, 903; 166/246; 405/128; 588/202, 203

[56] References Cited

U.S. PATENT DOCUMENTS

| | | |
|---|---|---|
| 5,384,048 | 1/1995 | Hazen et al. . |
| 5,538,530 | 7/1996 | Heaton et al. . |
| 5,616,162 | 4/1997 | Crawford et al. ............................ 71/9 |
| 5,711,020 | 1/1998 | Wolfe et al. . |

FOREIGN PATENT DOCUMENTS

| | | |
|---|---|---|
| 0 589 818 | 3/1994 | European Pat. Off. . |
| 40 36 787 | 5/1992 | Germany . |

OTHER PUBLICATIONS

Field et al. 'Oxidation of anthracene in water/solvent mixtures by the white–rot fungus, Bjerkandera sp. strain BOS55.' Appl. Microbiol. Biotechnol. vol. 44 (1994), pp. 234–240.
"Waste Management: Microorganisms that Take on Dirty Jobs", Industries in Transitions, May 1, 1996.
"Bioremediation's value as opposed to the value of chemical techniques is debated; US bioremediation market estimated at $1.5 bil in 1996", Chemical Marketing Reporter, p. SR14, Apr. 14, 1997.
"Cleaning up contaminated soils", BioCycle, vol. 36, pp. 40–41, May 1, 1995–May 31, 1995.
"Clean up at munitions sites", BioCycle, vol. 37, pp. 49–50, Mar. 1, 1996–Mar. 31, 1996.
Cacciatore, D., et al., "Principles of soil bioremediation", Biocycle, vol. 36, pp. 61–64, Oct. 1, 1995–Oct. 31, 1995.
Zodrow, J., "Second generation, in situ bioremediation: Enzymes, super–bugs and geobotany", Environmental Solutions, p. 20, Feb. 1, 1997–Feb. 28, 1997.
Shevlin, P., et al., "In situ recycling of contaminated soil uses bioremediation", Pipeline & Gas Journal, vol. 223, p. 51, Apr. 1, 1996–Apr. 30, 1996.
Won, W. D., et al., "Toxicity and Mutagenicity of 2,4, 6–Trinitrotoluene and Its Microbial Metabolites", Appl. Environ. Microbiol., 31:576–580 (1976).
Williams, R. T., et al., "Composting of Explosives and Propellant Contaminated Soils Under Thermophilic and Mesophilic Conditions", J. Ind. Microbiol., 9:137–144 (1992).

Kaplan, D. L., et al., "Thermophilic Biotransformations of 2,4,6–Trinitrotoluene Under Simulated Composting Conditions", Appl. Environ. Microbiol., 44:757–760 (1982).
Funk, S. B., et al., "Initial–Phase Optimization for Bioremediation of Munition Compound–Contaminated Soils", Appl. Environ. Microbiol., 59 (7) :2171–2177 (1993).
Preuss, A., et al., "Anaerobic Transformation of 2,4,6–Trinitrotoluene (TNT)", Arch. Microbiol., 159:345–353 (1993).
Boopathy, R., et al., "Anaerobic Removal of 2,4,6–Trinitrotoluene (TNT) Under Different Electron Accepting Conditions: Laboratory Study", Wat. Environ. Res., 65(3) :271–275 (1993).
Collie, S. L., et al., "Degradation of 2,4,6–Trinitrotoluene (TNT) In An Aerobic Reactor", Chemosphere, 31 (4) : 3025–3032 (1995).
Zappi, M. E., et al., "Aerobic Treatment of Explosives–Contaminated Soils Using Two Engineering Approaches", Bioremed. Recalc. Org., pp. 281–288 (1995).
Bradley, P. M., et al., "Factors Affecting Microbial 2,4, 6–Trinitrotoluene Mineralization in Contaminated Soil", Environ. Sci. Technol., 29:802–806 (1995).
Breitung, J., et al., "Bioremediation of 2,4,6–Trinitrotoluene–Contaminated Soils By Two Different Aerated Compost Systems", Appl. Microbiol. Biotechnol., 44:795–800 (1996).
Bae, B. H., et al., "Aerobic Biotransformation and Mineralization of 2,4,6–Trinitrotoluene", Bioremed. Recalc. Org., pp. 231–237 (1995).
Soeder, C.J., et al., "Influence of Phytogenic Surfactants (Quillaya Saponin and Soya Lecithin) on Bio–Elimination of Phenanthrene and Fluoranthene by Three Bacteria", Appl. Microbiol. Biotechnol., 44:654–659 (1996).
Document No. EPA/625/R–93/013 entitled "Approaches for the Remediation of Federal Facility Sites Contaminated with Explosive or Radioactive Wastes", p. 51 (Sep. 1993).
Jenkins, T.F., et al., "Comparison of Extraction Techniques for Munitions Residues in Soil", Anal. Chem., 59 (9) :1326–1331 (1987).
U.S. Army Environmental Center Report No. CETHA–TS–CR–93043, Contractor No. DACA31–91–D–0079, Task Order No. 01 (Aug. 1993).

(List continued on next page.)

Primary Examiner—William H. Beisner
Attorney, Agent, or Firm—Klaas Law O'Meara & Malkin

[57] ABSTRACT

An efficient method for decontaminating soil containing organic explosives ("TNT" and others) in the form of solid portions or chunks which are not ordinarily subject to effective bacterial degradation. The contaminated soil is treated by delivering an organic solvent to the soil which is capable of dissolving the explosives. This process makes the explosives more bioavailable to natural bacteria in the soil which can decompose the explosives. An organic nutrient composition is also preferably added to facilitate decomposition and yield a compost product. After dissolution, the explosives are allowed to remain in the soil until they are decomposed by the bacteria. Decomposition occurs directly in the soil which avoids the need to remove both the explosives and the solvents (which either evaporate or are decomposed by the bacteria). Decomposition is directly facilitated by the solvent pre-treatment process described above which enables rapid bacterial remediation of the soil.

17 Claims, 2 Drawing Sheets

OTHER PUBLICATIONS

Boopathy, R., et al., "Nitroaromatic Compounds Serve as Nitrogen Source for Desulfovibrio sp. (B Strain)", *Can. J. Microbiol.*, 39:430–433 (1993).

Grant, C. L., "Holding–Time Estimates For Soils Containing Explosives Residues: Comparison Of Fortification Vs. Field Contamination", *Environ. Toxicol. Chem.*, 14(11):1865–1874 (1995).

Isbister, J.D., et al. "Composting For Decontamination Of Soils Containing Explosives", Microbiologica, 7:47–73 (1984).

Daniels, Jeffrey I., et al. "Human Health Risks From TNT, RDX, And HMX In Environmental Media And Consideration Of The U.S. Regulatory Environment", Proceedings 1994 Luxembourg International Symposium on the Rehabilitation of Former Military Sites and Demilitarization of Explosive Oordnance (Nov. 14 to 18, 1994).

METHOD FOR THE DECONTAMINATION OF SOIL CONTAINING SOLID ORGANIC EXPLOSIVES THEREIN

RELATED APPLICATION

This application claims priority from provisional application Ser. No. 60/047,280 filed May 21, 1997.

CONTRACTUAL ORIGIN OF THE INVENTION

The United States has rights in this invention pursuant to Contract No. DE-AC07-94ID13223 between the U.S. Department of Energy and Lockheed Martin Idaho Technologies Company.

BACKGROUND OF THE INVENTION

The present invention generally relates to the decontamination of soil materials containing solid organic explosives therein, and more particularly to a high efficiency process for removing solid portions of organic explosive compounds from contaminated soil using a specialized multi-step bioremediation procedure.

Environmental decontamination programs often require the removal of chemical contaminants from soil-containing regions over wide geographical areas. Of particular importance is the elimination of explosive compositions from soil materials, with particular emphasis on solid organic explosives including but not limited to trinitrotoluene ("TNT"), trimethylenetrinitronitramine ("RDX"), and tetramethylenetetranitramine ("HMX"), as well as other nitramine and nitroaromatic explosive materials. As discussed further below, the present invention shall not be restricted to the removal of any particular organic explosive materials. Likewise, the term "solid organic explosive" as used herein shall involve carbon containing compositions that are chemically capable of exploding or otherwise detonating for commercial, military, and/or other purposes. The presence of these compositions within soil materials (particularly in the form of large individual portions or "chunks") can occur at numerous locations including military installations, ordinance factories, chemical/explosive processing plants, and sites where munitions have been detonated as part of a military conflict or ordinance testing program. In particular, solid organic explosives may be present as raw waste products obtained from, for example, manufacturing plants or can also consist of unexploded (or partially exploded) munitions. Residual organic explosives can cause a number of health and safety problems if such materials are allowed to remain within the soil in an untreated state.

Regardless of the particular size parameters associated with residual organic explosives in contaminated soil materials (which will be discussed in considerable detail below), the presence of these compositions can again have serious ecotoxicological consequences. These consequences are typically manifested in many undesired effects and conditions which are generally exemplified in Won, W. D., et al., "Toxicity and Mutagenicity of 2,4,6-Trinitrotoluene and Its Microbial Metabolites", *Appl. Environ. Microbiol.*, 31:576–580 (1976). For example, the adverse effects of organic explosive contamination include but are not limited to toxicity to algae, copepods, oyster larvae, and a generally high level of mutagenicity. A substantial interest therefore exists in the development of an effective, economical, and environmentally-compatible method for eliminating residual solid organic explosives from contaminated soil sites (particularly explosives in the form of large portions or chunks which present special difficulties as discussed below).

A number of prior decontamination methods have been developed which involve the use of microorganisms (e.g. bacteria) that are naturally present in the soil to digest, consume, and otherwise degrade various explosive materials. These bacterial processes (which are generally designated herein as "bioremediation" methods) are characterized by a number of very specific parameters, operating conditions, and procedures which will generally control the overall outcome of the treatment program being employed. For example, bioremediation systems have been used which involve conventional composting techniques. This approach is discussed in, for example, Williams, R. T., et al., "Composting of Explosives and Propellant Contaminated Soils Under Thermophilic and Mesophilic Conditions", *J. Ind. Microbiol.* 9:137–144 (1992). Other bacterial remediation methods which are applicable to the treatment of explosive-contaminated soil include the preparation of anaerobic bacteria slurries which are combined with the soil materials of concern as generally discussed in, for example, Funk, S. B., et al., "Initial-Phase Optimization for Bioremediation of Munition Compound-Contaminated Soil", *Appl. Environ. Microbiol.*, 59(7):2171–2177 (1993). Likewise, aerobic bacteria slurries have also been used to remove explosives from contaminated soil as outlined in a number of references including Bradley, P. M., et al., "Factors Affecting Microbial 2,4,6-Trinitrotoluene Mineralization in Contaminated Soil", *Environ. Sci. Technol.*, 29:802–806 (1995).

All of the techniques listed above involve a common basic procedure, namely, the use of microorganisms (e.g. bacteria) in either an anaerobic or aerobic state to treat the soil materials of interest so that residual solid explosive compositions are digested and removed by the bacteria. However, the use of composting methods offers considerable promise for a variety of reasons including an increased degree of simplicity, lower cost and labor requirements, and environmental compatibility. Composting processes are also applicable to many different explosive materials and again employ natural soil bacteria. While composting methods offer many important benefits (and are therefore the focus of the present invention), traditional composting systems normally experience a substantial loss of efficiency when the removal of large portions or "chunks" of organic explosives is required. Specifically, in standard composting systems, increases in the overall size (e.g. weight) of the explosive portions to be treated will result in decreased and often incomplete (or very slow) remediation. While it is not possible to provide exact size parameters which cause losses in composting efficiency for all situations, such problems will typically result when explosive portions are treated which weigh at least about 0.01 grams or more. Further numerical data involving size and weight parameters which cause difficulties in traditional composting systems will be presented below in the Detailed Description of Preferred Embodiments section.

As the overall size and weight of the explosive portions increases, a loss in bioremediation efficiency typically occurs because these materials are generally less "available" (or "bioavailable") to the bacteria. The terms "available", "availability", "bioavailable", and "bioavailability" as used herein involve the ability of bacteria to consume and otherwise digest the explosives under consideration which is substantially influenced by the physical parameters of the explosive portions including their size, density, degree of agglomeration, weight, and other related factors. Solid organic explosives that are present in a large chunk-like state are often too large and dense to enable effective bacterial consumption of these materials using conventional composting techniques. Thus, the bio-conversion of solid organic explosives by soil-borne bacteria occurs according to the general bioavailability of these materials which, in turn, is a function of the physical parameters of the explosive portions in question. All of these factors combine to generally define a process known as mass transfers which involves the availability and overall conversion capacity of the bacterial system(s) under consideration based on the physical state of the materials being treated.

The overall availability (e.g. bioavailability) of soil-dispersed organic explosives in bioremediation systems is typically controlled by the extent to which the explosives are dissolved within the soil. A greater degree of explosive dissolution and homogeneous dispersion of these materials will typically improve bioavailability levels and composting efficiency. For example, agitation of the soil materials being treated, as well as the use of surfactant compositions have been employed to improve the bioremediation process. The addition of surfactant compositions for this purpose is discussed in, for example, Zappi, M. E., et al., "Aerobic Treatment of Explosives-Contaminated Soils Using Two Engineering Approaches", *Bioremed. Recalc. Org.*, pp. 281–288 (1995). According to this reference, the addition of a specific commercial surfactant sold under the trademark "TWEEN 80" at a 3% by weight amount (relative to the amount of dry contaminated soil) increased the consumption rate of waste TNT in a continuously-stirred aqueous reactor system. Similar results were achieved through the use of polycyclic aromatic hydrocarbon-based surfactants as discussed in Soeder, C. J., et al., "Influence of Phytogenic Surfactants (Quillaya Saponin and Soya Lecithin) on Bio-Elimination of Phenanthrene and Fluoranthene by Three Bacteria", *Appl. Microbiol. Biotechnol.*, 44:654–659 (1996).

In addition to the use of biological (e.g. bacteria-based) decontamination systems, various non-biological methods have been employed in connection with explosive-contaminated soil including solvent-extraction techniques. For example, laboratory and pilot-scale tests involving the use of acetone applied to explosive-contaminated soils are discussed in a document prepared by the U.S. Environmental Protection Agency (No. EPA/625/R-93/013) entitled "Approaches for the Remediation of Federal Facility Sites Contaminated with Explosive or Radioactive Wastes", Vol. 51 (September 1993). As noted above, this particular testing program did not employ a bacteria-based composting system in which explosive materials were permitted to remain in the soil for bioremediation. Instead, the solvent (e.g. acetone) was simply used as an extractant. The acetone was applied to the soil and thereafter removed in explosive-laden form. In this type of system, the resulting product removed from the soil is a hazardous waste solvent composition containing dissolved explosives therein. Thus, a detrimental characteristic of solvent-extraction systems is the production of another waste product (e.g. the explosive-laden waste solvent) which creates substantial storage, disposal, and treatment problems. In fact, an entirely safe recovery method for the explosive-laden waste solvents that are generated during conventional extraction procedures has not yet been found, with the resulting contaminated product representing a hazardous waste material.

A final method for treating explosive-contaminated soil involves the use of physical separation methods including but not limited to the manual screening of soil materials to remove explosive portions of a selected size. Not only is this process slow and labor-intensive, but it creates additional hazardous waste (e.g. explosive chunks) materials which must be further processed.

Accordingly, prior to the development of the present invention, a need remained for a safe, effective, environmentally-conscious, and cost-efficient method for treating soil containing solid organic explosives (especially in large portions or "chunks" as further defined below.) The claimed invention satisfies this need by providing a unique process which employs a distinctive, novel, and highly-effective combination of multiple technologies. The process described below avoids (A) the generation of explosive-laden hazardous waste products which are generated by solvent-extraction methods; and (B) the difficulties associated with composting methods when large portions or chunks of explosive materials are treated, namely, the inability of soil bacteria to degrade such materials over a reasonable amount of time (if at all) due to bioavailability problems. The invention offers a number of key benefits including (1) the ability to decontaminate large quantities of organic explosive-containing soil notwithstanding the presence of explosive portions therein of a large size that are not normally treatable in an effective manner by traditional bioremediation methods; (2) a considerable improvement in the ability of the soil bacteria to metabolize the desired explosive compounds (regardless of the physical form of such materials); (3) the avoidance of any process steps which generate hazardous waste by-products that require further treatment, disposal, or storage (including contaminated explosive-laden waste solvents); (4) the capability to conduct on-site remediation at a wide variety of geographical locations using a minimal amount of equipment and labor; and (5) the general ability to effectively treat organic explosive-contaminated soil in a manner which is environmentally compatible, rapid, and cost-effective. In accordance with these benefits and the unique combination of process steps described in detail below, the present invention represents an advance in the art of soil decontamination and bioremediation technology.

SUMMARY OF THE INVENTION

It is an object of the present invention to provide a highly-efficient bioremediation (e.g. microorganism-based) system for removing solid organic explosives from soil materials so that the soil can be effectively decontaminated.

It is another object of the invention to provide a bioremediation system which is able to remove solid organic explosives from soil materials ranging from powder-type granules having small particle sizes to large individual units (e.g "chunks") that would not be subject to effective microbiological/ bacterial consumption using standard composting methods.

It is another object of the invention to provide a bioremediation system for the elimination of solid organic explosives from soil materials which substantially improves the ability of natural soil-borne bacteria to metabolize the explosives by increasing the overall bioavailability levels of these compositions.

It is another object of the invention to provide a bioremediation system for the elimination of solid organic explosives from soil materials which avoids the generation of hazardous waste by-products including explosive-laden solvents which are produced from conventional solvent-extraction techniques.

It is a further object of the invention to provide a bioremediation system for the elimination of solid organic explosives from soil materials which is safe, effective, and enables the return of treated soil samples directly to the environment.

It is a further object of the invention to provide a bioremediation system for the elimination of solid organic explosives from soil materials which is cost efficient, non-labor-intensive, and requires minimal amounts of added reagents and supplemental ingredients.

It is an even further object of the invention to provide a bioremediation system for the elimination of solid organic explosives from soil materials which enables the remediation process to occur in a very rapid time frame compared with conventional biological processing systems.

It is an even further object of the invention to provide a bioremediation system for the elimination of solid organic explosives from soil materials which involves a novel combination of process steps using multiple technologies that substantially improves the treatment process.

A brief overview of the claimed invention will now be provided. More specific details and enabling information will be presented below in the Detailed Description of Preferred Embodiments section. The process described herein involves a unique, effective, and environmentally-conscious method for removing waste (e.g. residual) solid organic explosive compositions from soil materials. As discussed above, the term "solid organic explosive" shall not be restricted to any particular compositions and is defined herein to encompass carbon containing compositions that are chemically capable of exploding or otherwise detonating for commercial, military, and/or other purposes. Representative solid organic explosive materials which may be effectively removed from soil materials using the claimed method include but are not limited to trinitrotoluene ("TNT"), trimethylenetrinitronitramine ("RDX"), and tetramethylene-tetranitramine ("HMX"), as well as other nitramine and nitroaromatic explosive compounds.

As will become readily apparent from the discussion provided below, the method of the present invention may be used to eliminate solid organic explosive compositions which range in size and mass from small dust-like particles to larger portions of material. The claimed process is especially useful in removing solid organic explosives which are present in the form of large portions or "chunks" that (in view of their size/mass characteristics) would not be effectively consumable by natural soil-borne bacteria in traditional composting systems. While the present invention shall not be restricted to the removal of explosive portions having any specific size parameters, it is particularly effective in eliminating explosive portions or chunks having a mass (weight) of at least about 0.01 grams or more. Further information regarding the size parameters of the explosive portions which may be removed using the claimed process (and are not subject to effective removal using conventional composting methods) will be provided below in the Detailed Description of Preferred Embodiments section.

As previously discussed, the presence of solid organic explosives in soil (particularly in large portions) can cause a wide variety of health and safety problems. For this reason, the effective decontamination of explosive-containing soil at various sites (including but not limited to military installations, munitions factories, artillery ranges, and the like) is of considerable importance. The procedure outlined below constitutes a highly effective method for eliminating solid organic explosives from contaminated soil which employs a unique combination of biological and non-biological techniques. These multiple technologies complement each other and create a versatile decontamination system which enables the bioremediation of explosive-containing soil in an entirely novel manner.

The claimed system initially involves the step of providing a supply of soil containing at least one solid organic explosive composition therein. Representative and non limiting explosive compositions which may be effectively removed from the soil again include but are not limited to trinitrotoluene ("TNT"), trimethylenetrinitronitramine ("RDX"), and tetramethylene-tetranitramine ("HMX"), as well as other nitramine and nitroaromatic explosive compounds. It is important to emphasize that the bioremediation method described herein shall not be restricted to the elimination of solid organic explosives having any particular size or mass parameters. The process may be used with a high degree of effectiveness in removing explosive materials ranging from small dust-size particles to large portions or chunks which would not normally be degradable by conventional bacterial systems. While more detailed data will be presented below involving the size parameters of the organic explosive compositions that are most suitable for treatment using the claimed process, it is particularly effective in treating portions of organic explosive material which weigh at least about 0.01 grams or more. These large materials are not effectively eliminated using standard composting methods, and it is therefore an advantage of the present invention that such materials can be efficiently treated regardless of their size. As discussed in greater detail below, this novel capability is a direct result of the unique process steps employed in the present method which represent a substantial departure from conventional bioremediation technology.

It should also be noted that the claimed method will effectively treat contaminated soil materials with varying amounts of solid organic explosives therein, with most of the soil materials of primary interest that are effectively treated using the present invention containing about 0.01–10% by weight total solid organic explosive compositions therein. However, this amount will necessarily vary based on many factors including the prior use of the soil under consideration and the overall degree of soil contamination.

To effectively remove solid organic explosives from soil materials in accordance with the invention, a supply of contaminated soil is first selected for treatment. As discussed in considerable detail below, the soil will contain a substantial amount of natural bacteria therein which are capable of metabolically degrading/consuming the solid organic explosive materials. Furthermore, the bioavailability of these explosive compositions is substantially increased using the special process steps summarized below. Additional information regarding the types of bacteria that are naturally present in soil which can consume organic explosive compounds will be presented in the Detailed Description of Preferred Embodiments section.

To accomplish bioremediation in accordance with the claimed invention, at least one organic solvent is delivered to the soil which is of a type that is capable of at least partially dissolving the solid organic explosive compositions in the soil. Delivery of the organic solvent to the soil causes it to come in direct physical contact with the explosive compositions therein. As a result, the explosive materials at least partially (and, in most cases entirely) dissolve, thereby causing solubilization and "redistribution" of the explosive compounds within the soil (particularly the large portions or "chunks" discussed above). In accordance with this dissolution process, the explosive compositions become more bioavailable to the natural bacteria in the soil which are then able to consume them with increased efficiency. The present invention shall not be limited to any particular organic solvents provided that they are able to solubilize solid organic explosives of the general type discussed herein. Representative and non-limiting organic solvents which may be employed for this purpose include but are not limited to acetone, pyridine, n,n-dimethylformamide, dimethylsulfoxide, 1-methyl-2-pyrrolidinone, methyl acetate, benzene, toluene, isobutyl acetate, methanol, ethanol, and mixtures thereof. However, acetone (alone or combined with other organic solvents) is preferred for a variety of reasons including the ability of many bacteria to readily digest this material and its efficiency in dissolving the explosive materials of interest. While the claimed procedure shall not be restricted to any particular amounts of organic solvent for the purposes outlined above (which may be determined in accordance with preliminary pilot testing), the selected organic solvent is preferably combined with the soil in a total amount equal to about 0.1–380 ml of the chosen organic solvent per kilogram of contaminated soil. This range apples to both a single solvent and a mixture of multiple solvents, with the soil weight being determined prior to the addition of any other ingredients.

The claimed invention (as discussed in considerable detail below) shall not be restricted to any procedure for combining the organic solvent and explosive-contaminated soil. A number of different methods are applicable ranging from in situ (e.g. "on-site") solvent delivery to the soil without removing the soil from the ground to physically removing selected amounts of soil (e.g. "soil samples") and placing them into a suitable containment vessel for treatment. Either method may be employed in accordance with the basic procedures and inventive steps indicated in the next section. However, for the sake of clarity, the present invention will be described herein with primary reference to approaches which involve the removal of soil samples and treatment thereof in a selected containment vessel.

In addition to the application of an organic solvent to the explosive-contaminated soil, a preferred embodiment of the invention will also involve the delivery of at least one or more organic nutrient compositions to the soil. The term "organic nutrient composition" as used herein shall encompass carbonaceous materials which may be utilized by the natural soil bacteria as an energy/nutrition source to form a completed compost product. Many different organic nutrient compositions may be employed for this purpose (alone or in mixtures). Exemplary and non-limiting organic nutrient compositions which can be used as an energy source for the natural explosive-degrading bacteria in the soil include but are not limited to animal manure (e.g. cow or chicken droppings), sawdust, alfalfa, potatoes, wood chips, lettuce, sugar beet waste, ground corn cobs, and mixtures thereof. The invention shall not be restricted to any particular types or quantities of these materials which shall be determined in accordance with preliminary pilot studies involving the soil being treated. However, in a representative embodiment, effective results will be achieved if approximately 4–6 kilograms of the selected organic nutrient composition are added per kilogram of contaminated soil. This range apples to both a single nutrient or a mixture of multiple nutrients, with the soil weight being determined prior to the addition of any other ingredients. It is also important to emphasize that addition of the organic nutrient composition(s) to the soil may be undertaken before or after delivery of the organic solvent, with both alternatives being considered equivalent and covered under the specific claim language presented herein.

Furthermore, in accordance with the chemical and biological processes involved in the present invention, the addition of one or more organic nutrient compositions shall not always be considered an absolute requirement. The natural bacteria in substantially all soil materials are capable of degrading solid organic explosives in the absence of any added nutrients (although this process may occur at a slow or ineffective rate). The need for nutrient supplementation will ultimately depend on the carbon content of the soil, the explosives being degraded, the type/amount of bacteria in the soil, and other related factors as again determined by routine preliminary testing. For example, "peat"-type soil materials with considerable amounts of residual vegetable/animal matter therein in the form of manure, waste vegetation, and the like (e.g. 50% by weight or more of these materials in combination) may not require the addition of a separate carbonaceous nutrient. However, to ensure effective bioremediation and to avoid the need for preliminary carbon-content testing on the soil materials of interest, it is preferred that at least one organic nutrient composition be added to the soil as a default process step unless otherwise indicated in accordance with preliminary research.

At this point (e.g. after combination of the explosive-contaminated soil with the organic solvent and the organic nutrient composition [if used]), the resulting mixture will consist of a novel compost product that is used to remove the solid organic explosive compositions therefrom by bacterial degradation. It should be emphasized that the compost product is capable of eliminating solid organic explosive materials which were initially present in the form of large portions or "chunks" having the size parameters discussed above. These materials are not normally degraded in an effective manner by conventional composting techniques which do not employ the claimed solvent pre-treatment stage.

As previously noted, addition of the organic solvent to the soil causes a solubilization of the explosive compounds (including the large portions or "chunks") so that such materials dissolve and are "redistributed" within the soil/compost matrix. In accordance with this process, the explosive materials are made more "bioavailable" to the bacteria so that effective bioremediation can occur. At this stage, the claimed process substantially departs from prior solvent-based extraction systems in an important and significant manner. Instead of removing the solvent and dissolved explosive compositions therein (followed by disposal, storage, or subsequent treatment of such materials which is undesirable from a cost, safety, and efficiency standpoint), a different approach is taken. In the present system, the explosive materials (after dissolution) are allowed to remain within the soil/compost matrix for a time period sufficient to allow the natural soil-borne bacteria to chemically break down (e.g. digest/metabolize) the explosive compositions directly within the soil. Specifically, the explosive materials are maintained (e.g. left) within the compost product/soil for bacterial consumption. Explosive consumption is accomplished by the bacteria over a rapid time period of not more than about 15 days (about 5–10 days in most situations). The required time period will vary based on a variety of factors including type of explosive being consumed, the level of soil contamination, and other related factors. The applicable time period is substantially shorter compared with prior composting systems which do not employ the unique process steps listed above including the use of a solvent pre-treatment stage. This is particularly true in connection with the treatment of soil containing large portions or "chunks" of organic explosives that are not subject to effective bioremediation using standard composting methods. Effective metabolic consumption of chunk-type and other explosive materials in the claimed process is accomplished in accordance with the preliminary solvent treatment stage (e.g. "solvent pre-treatment"). This step again increases the bioavailability of the explosive compounds to the soil-borne bacteria through the effective dissolution and "redistribution" of such materials. Likewise, it should also be noted that the process discussed herein also facilitates metabolic consumption of the explosive materials by natural protozoa and fungi within the soil (in addition to bacterial degradation).

Regarding the organic solvents employed in the claimed process, they are eliminated through spontaneous evaporation from the soil (due to the volatile nature thereof) and/or are metabolically consumed by the natural soil bacteria (including but not limited to the same bacteria which are used to consume the organic explosive materials.) It is therefore another important feature of the claimed process (which is distinctive from conventional solvent-extraction techniques) that the solvent materials added to the soil do not have to be physically removed from the soil after dissolution of the organic explosives. The removal of such materials (which is undertaken in standard solvent-extraction methods) creates storage, disposal, and other problems that are effectively avoided by the present invention.

In accordance with the process discussed above, the explosive compositions previously in the soil (including those in large portion or "chunk" form) are eliminated by bacterial conversion into other, non-explosive (and non-toxic) metabolic reaction products including various amines. The detoxified soil may then be returned to the environment from which it came, with the treated soil being suitable for a wide variety of commercial, recreational, and other uses without limitation.

The claimed process again involves an efficient biological treatment method for organic explosives (particularly those in large portions) which synergistically employs multiple technologies in a novel manner to solve a soil contamination problem of considerable importance. This problem specifically involves the removal of solid organic explosive portions or "chunks" from the soil which are sufficiently large to render them "unavailable" to soil bacteria in conventional composting systems. Accordingly, the present invention represents an important advance in decontamination technology which avoids the bioavailability problems associated with standard composting techniques and likewise eliminates the production of explosive-laden solvent materials that are generated when conventional solvent-extraction methods are employed. These and other objects, features, and advantages of the invention shall be discussed in greater detail below in the following Brief Description of the Drawings and Detailed Description of Preferred Embodiments sections.

DETAILED DESCRIPTION OF PREFERRED EMBODIMENTS

In accordance with the present invention, a unique and highly-effective procedure is disclosed for eliminating solid organic explosive compositions from contaminated soil, with particular emphasis on soil materials that contain large portions or "chunks" of organic explosives which are not effectively eliminated in conventional bioremediation systems. Explosive-containing soil can again exist at many different geographical sites ranging from military installations to ordinance factories and artillery ranges. The claimed system is therefore highly beneficial from a health, safety, environmental, and economic standpoint since the treated soil can be returned to its point of origin and reused without restriction for a wide variety of commercial, recreational, and other purposes.

As previously indicated, the present invention offers considerable advantages and a substantial degree of improvement over traditional decontamination methods including (1) conventional bacterial treatment processes (which cannot effectively eliminate explosive compositions in large portions or "chunks"); (2) solvent-extraction methods in which explosive-laden solvent materials are removed from the soil which are hazardous and difficult to treat; and (3) physical separation methods using sieve or screen-like structures in a slow and labor-intensive process to manually extract large portions of explosive material from the soil (which are subject to further disposal requirements). The procedure described below involves a unique approach which provides rapid and effective results regardless of the size parameters associated with the explosive materials, avoids the disadvantages listed above, and completely eliminates the explosive compounds of interest so that further treatment is not needed. These and other benefits associated with the invention will become readily apparent from the following detailed description of the claimed process and its various attributes. As a further point of information, it should be noted that the inventive method summarized below shall not be restricted to any particular reagents, processing environments, handling requirements, soil materials, or numerical parameters unless otherwise indicated herein. All specific examples of operational parameters, reagents, and other features of the claimed process which are listed in this section represent preferred embodiments and shall not limit the invention in any respect. In order to fully explain the novel characteristics and benefits listed above, the following detailed discussion is provided.

Figure 1:
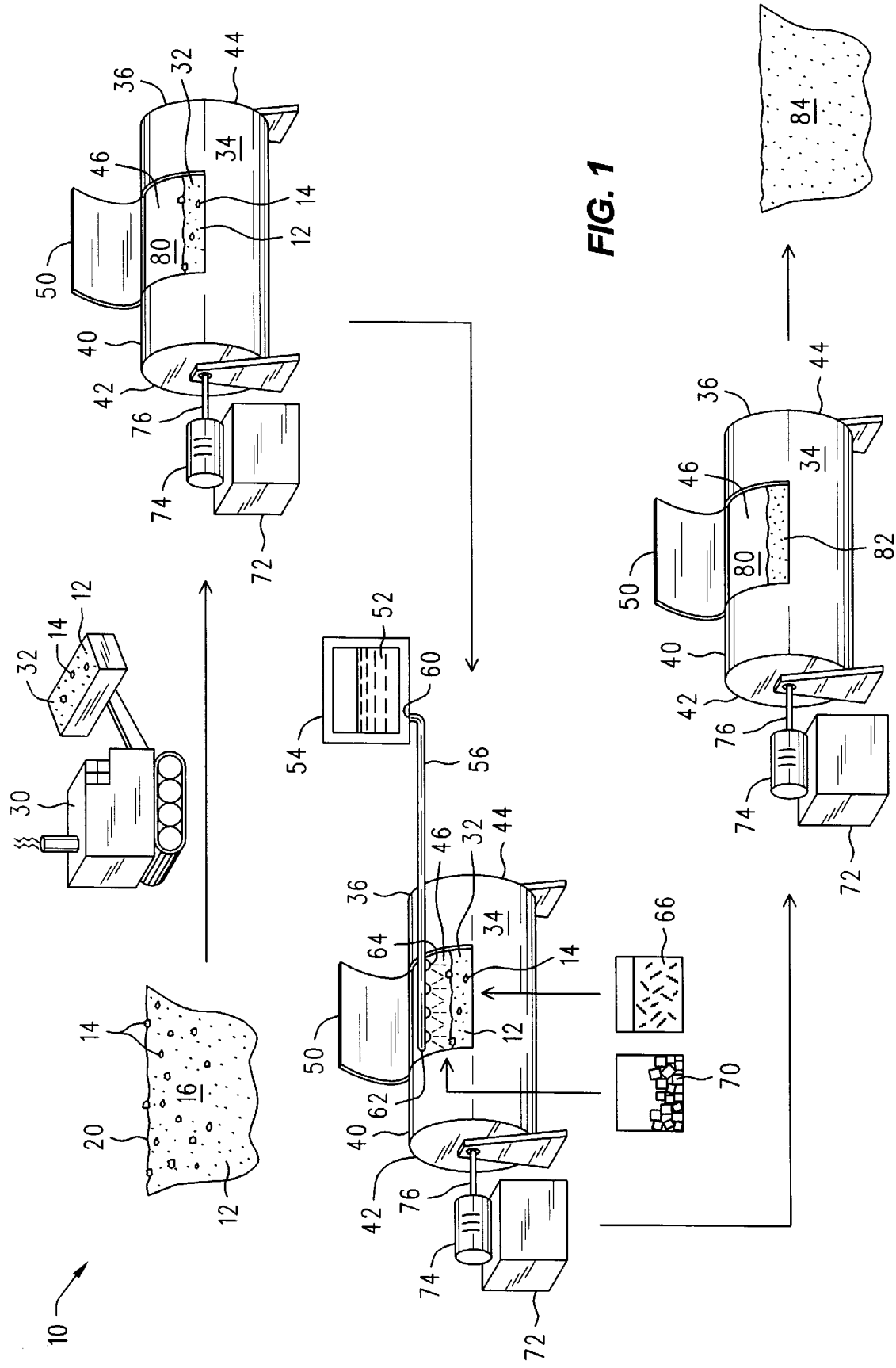
FIG. 1 is a schematic representation of the basic process steps which are used in accordance with the present invention to biologically remove solid organic explosive compositions in large portions or "chunks" from contaminated soil in a safe, rapid, and effective manner.

With reference to FIG. 1, an exemplary explosive-contaminated site 10 is schematically illustrated. The site 10 may involve, without limitation, a number of different geographic locations and regions ranging from military installations to abandoned proving grounds, explosive factories/processing plants, artillery ranges, and sites where munitions have been detonated as part of a military conflict or ordinance testing program. The waste or "residual" explosive materials to be eliminated from the site 10 (discussed in detail below) may be derived from, for example, unexploded or partially-exploded ordinance and products left over from chemical/explosive processing plants. Accordingly, the present invention shall be applicable to soil regions and land sites which contain solid explosives therein from any source regardless of their age, level of decontamination, and soil type.

With continued reference to FIG. 1, the site 10 includes explosive-contaminated soil 12 therein. The soil 12 contains solid organic explosive materials which range in size from small dust-like particles having weight (mass) values in the microgram/nanogram range to much larger portions which are the main focus of this invention. The claimed method can effectively process and eliminate all of the explosive materials in the soil 12 regardless of the size parameters associated therewith (including the dust-like particles mentioned above). However, the process of the invention departs from conventional bioremediation techniques in its ability to effectively and rapidly treat much larger portions or "chunks" of explosive material. The procedure described herein can treat a variety of different soil samples without restriction to any given explosive concentration level. For example, the present invention is able to treat soil 12 which contains about 0.01–10% by weight total solid organic explosive materials therein, with these values representing a preferred and non-limiting range of primary interest. In general, the amount of a given explosive composition in a soil sample will depend on the prior use of the soil and whether it has been subject to any previous treatment measures.

The test sites of main interest (from a health and ecotoxicology standpoint) involve those which contain large portions or "chunks" of organic explosive materials which are schematically represented in FIG. 1 at reference number 14 in the soil 12 of contaminated site 10. The portions 14 (and other explosive compositions of interest) may be buried within the interior regions 16 of the soil 12, typically as far as about 1–48 inches from the surface 20 of the soil 12 at the contaminated site 10. Alternatively, the portions 14 of explosive material may be located directly at and extending through the surface 20 of the soil 12. For reference purposes, the term "solid organic explosive composition" shall again be broadly construed and defined to involve carbon-containing compositions that are chemically capable of exploding or otherwise detonating for commercial, military, and/or other purposes. While the present invention shall not be restricted to the elimination of any particular explosive compounds, representative solid organic explosive materials which may be effectively removed from soil materials using the claimed process include but are not limited to trinitrotoluene ("TNT"), trimethylenetrinitronitramine ("RDX"), and tetramethylenetetranitramine ("HMX"), as well as other nitramine and nitroaromatic explosive compounds.

With reference to the schematic illustration of FIG. 1, the soil 12 at the contaminated site 10 (as well as substantially all soil materials whether contaminated or not) will contain natural soil-borne bacteria therein which are capable of biodegrading and otherwise metabolically consuming a broad spectrum of carbon-containing materials including the solid organic explosives described above. The soil-borne bacteria are not shown in FIG. 1 due to the microscopic size characteristics of these organisms. The solid organic explosive materials in the soil 12 (including the large portions 14 thereof) are metabolically converted by the bacteria in the claimed process to various non-toxic by-products in a novel composting environment as discussed further below. Regarding the natural bacteria which reside within the soil 12 (and other soil materials), many different types and concentrations are present. Exemplary species of these bacteria include but are not limited to Pseudomonas, Mycobacterium, Clostridium, Streptomyces, Morganella, Providencia, Citrobacter, Methanococcus, Rhodococcus, Serratia, Stenotrophomonas, and others. The bacteria which reside in the soil 12 are not only able to digest solid organic explosive materials, but (in most cases) are likewise capable of substantially consuming the selected solvents that are employed in the claimed process as discussed further below.

Notwithstanding the natural bacteria which are present in the soil 12 and their ability of biodegrade waste carbonaceous materials including organic explosive compounds, the presence of such compounds in large portions or "chunks" (including the portions 14 shown in FIG. 1) can present considerable problems in conventional composting systems. As the overall size and weight of the explosive portions increases, a loss in bioremediation efficiency typically occurs since these materials are generally less "available" (or "bioavailable") to the organisms. The terms "available", "availability", "bioavailable", and "bioavailability" as used herein all involve the ability of the bacteria to consume and otherwise digest the explosives under consideration. This ability is substantially influenced by the physical parameters of the explosive portions including their size, density, degree of agglomeration, weight, and other factors that would normally inhibit bacterial degradation. Solid organic explosives which are present in a large "chunk-like" state are often too large and dense to enable effective bacterial consumption of these materials using conventional composting techniques as previously noted. Explosive products which are present in the form of sizeable portions or chunks may be too large and dense to allow the bacteria to effectively consume the explosive (e.g. reach the inner regions of any given explosive portion or chunk) over a reasonable time period. Thus, the bio-conversion of solid organic explosives by soil-borne bacteria occurs according to the general bioavailability of these materials which, in turn, is a function of the size/weight parameters of the explosive portions in question. All of these factors combine to generally define a process known as "mass transfer" which involves the bioavailability and overall conversion capacity of the bacterial system(s) under consideration based on the physical state of the compounds being treated.

As discussed in this section, it is a main goal and inventive feature of the claimed process to make the large portions 14 of organic explosive material illustrated in FIG. 1 more bioavailable to the bacteria in the soil 12. The soil 12 can then be decontaminated in a safe and effective manner without the creation of explosive-containing by-products which result when standard solvent-extraction techniques are employed. This unique process is likewise accomplished in a manner which is totally compatible with the surrounding environment, is minimally labor-intensive, and is not substantially limited by the size, weight, or dimensional characteristics of the portions 14 of explosive material.

In accordance with FIG. 1, the portions 14 of solid organic explosive material are randomly dispersed within the interior regions 16 of the soil 12 and at the surface 20 thereof. The degree of dispersion associated with the portions 14 of explosive material and the general location/concentration thereof shall not restrict the functional capabilities of the invention in any manner. In most cases, the solid organic explosive materials (including the large portions 14 illustrated in FIG. 1) will be randomly distributed although, in certain situations, they may be present in various "pockets" or high-concentration regions (again depending on the previous uses of the soil 12 under consideration.) The degree of dispersion and overall depth of the explosive materials within the soil 12 will likewise depend on the degree to which the soil 12 has been "disturbed" by natural or man-made processes which could (if implemented) cause a mixing or other redistribution of the portions 14 of explosive material in soil 12.

The solid portions 14 (or "chunks") of organic explosive material may be present in a wide variety of different symmetrical and asymmetrical configurations, sizes, and shapes which are all effectively treated using the claimed process. In this regard, the invention shall not be restricted to the treatment of explosive portions 14 having any given size characteristics which may again range from dust-like particles in the microgram/nanogram weight category to large portions 14 which weigh many grams. The unique capacity of the invention and its ability to render solid organic explosive materials more bioavailable to soil-borne bacteria in composting environments is widely applicable to explosive compositions of differing size, mass, and shape without limitation. Nonetheless, the claimed process is particularly beneficial in its ability to biologically eliminate large portions 14 of solid organic explosive material which are not effectively treated (due to size-related bioavailability problems) in standard composting systems. In general, the present system is particularly novel and distinguishable over prior biological methods in its ability to rapidly eliminate (through bacterial consumption) portions 14 of solid organic explosive material which have a weight (e.g. mass) of at least about 0.01 grams or more (more typically about 0.01–10 grams). These materials again present efficiency problems in conventional compost-type or other bacterial remediation systems.

Figure 2:
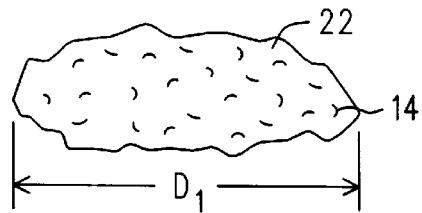
FIG. 2 is a schematic illustration (in substantially enlarged format) of a representative solid organic explosive portion or "chunk" which may be effectively dissolved and biologically eliminated in the specialized bioremediation system of the claimed invention.

While the novel benefits of the claimed process are most effectively demonstrated by its ability to process solid explosive materials having the large mass values listed above, these benefits can also be expressed with reference to portions 14 of explosive material having particular size parameters which would cause difficulties in conventional systems. For example, as shown in FIG. 2, an exemplary portion 14 (or "chunk") of an organic explosive material made from one or more of the compounds listed above is illustrated. While the invention shall not be restricted to the treatment of portions 14 having any particular size parameters as previously discussed, portions 14 which exceed certain size values are not effectively eliminated by bacterial consumption in standard bioremediation processes. Nonetheless, these materials are efficiently processed using the present system. With reference to FIG. 2, the claimed invention is particularly novel and distinguishable over prior biological systems in its ability to eliminate (through bacterial consumption) portions 14 of solid organic explosive material which have a diameter "$D_1$" of about 1–5 mm (or possibly more), with diameter "$D_1$" (also characterized as a "maximum diameter") being defined as the dimension of greatest value measured between any two points on the exterior surface 22 of the portion 14. In the example of FIG. 2, the diameter "$D_1$" involves the length of the portion 14 although, in other examples, it could represent the width, height, or thickness of the portion 14, depending on which of these values is the greatest. The above-listed values again represent dimensions associated with portions 14 of explosive material that are not effectively processed in conventional biological treatment systems due to bioavailability problems. While the mass and dimension values listed above shall not be considered limiting in any respect (with larger and smaller values likewise being applicable), these parameters represent preferred and most-commonly-encountered values which are treated in a much more rapid and effective manner compared with prior methods.

At this stage, the explosive-contaminated soil 12 at site 10 is treated using the process shown in FIG. 1. The claimed method shall not be restricted to any procedure for handling the explosive-contaminated soil 12 during bioremediation, with a number of different techniques being applicable ranging from (1) in situ (e.g. "on-site") treatment of the soil 12 directly in the ground without removing it from the site 10 to (2) physically removing selected amounts of the soil 12 (e.g. "soil samples") and placing them into a containment vessel (discussed below) for treatment. Either method may be employed in accordance with the basic procedures and inventive steps outlined herein. However, for the sake of clarity, the invention will be discussed below with reference to approaches which involve the removal of soil samples and treatment thereof in a separate containment vessel (method [2]). All of the information, parameters, materials, components, process steps, and other items listed below in connection with method (2) are equally applicable and incorporated by reference relative to method (1).

As shown in FIG. 1, a conventional piece of earth-moving equipment 30 (e.g. a bulldozer apparatus in large-scale decontamination projects or hand-operated implements in smaller remediation environments) is provided. The earth-moving equipment 30 is used to remove a selected quantity of soil 12 from the site 10. The process shown in FIG. 1 shall not be restricted to the treatment of any given quantity of soil 12 withdrawn from the site 10, with many different sampling sizes being applicable ranging from a few kilograms to thousands of kilograms depending on the overall size of the treatment vessel being employed and the particular remediation needs of the site 10. The numerical processing parameters listed below are prospectively applicable to all quantities of soil 12 selected for treatment, and are proportionately adjusted in accordance with the general guidelines expressed herein and discussed later in this section.

Once the selected amount of soil 12 is removed (e.g. in the form of a "soil sample" 32 shown schematically in FIG. 1), it is thereafter placed inside a treatment vessel 34 which may be configured in any size or shape. In a representative and non-limiting embodiment as illustrated in FIG. 1, the treatment vessel 34 will consist of a horizontal rotatable drum 36 constructed from any biologically inert materials (e.g. stainless steel and the like). In such a system, typical and preferred capacity values will be about 100–10,000 kilograms although this range is provided for example purposes only and may be widely varied depending on the processing needs under consideration. It is therefore important to emphasize that the containment vessel 34 illustrated in FIG. 1 is representative only and shall not limit the invention in any respect.

The vessel 34 (e.g. drum 36) will have a continuous side wall 40, a closed first end 42, and a closed second end 44. Positioned at an intermediate location within the side wall 40 between the first and second ends 42, 44 is an opening 46 which is covered by a sealable cover member 50 optimally made of the same materials employed in connection with the side wall 40 of the vessel 34. The vessel 34 is again sized to receive the soil sample 32 therein as shown in FIG. 1 which is delivered into the vessel 34 through the opening 46. Alternatively, either or both of the first and second ends 42, 44 may be constructed so that they can be opened on-demand with elimination of the opening 46 in the side wall 40 and cover member 50 associated therewith. Again, the illustrations shown in FIG. 1 are representative only and can be varied as needed and desired. At this stage, the soil sample 32 within the vessel 34 is ready for bioremediation.

Next, a supply of a selected organic solvent capable of at least partially and, in a preferred embodiment, entirely dissolving the portions 14 of solid organic explosive material within the soil sample 32 is directly applied to the sample 32 in the vessel 34. Many different methods may be employed for applying the solvent to the soil sample 32, with the claimed process not being restricted to any given procedure. One technique for delivering the solvent is illustrated in FIG. 1. Specifically, the solvent (schematically illustrated in FIG. 1 at reference number 52) is stored within a containment chamber 54 (e.g. made of stainless steel or other inert material) having a tubular conduit 56 attached thereto. The conduit 56 has a first end 60 operatively connected to the chamber 54 (and in fluid communication with the solvent 52 therein), and a second end 62 operatively connected to and in fluid communication with one or more spray heads 64 of conventional design. The spray heads 64 (and second end 62 of the conduit 56) are appropriately positioned over and above the opening 46 in the side wall 40 of the vessel 34 so that the solvent 52 can be readily delivered to the soil sample 32. In the alternative, the spray heads 64 may be eliminated so that the solvent 52 being supplied from the second end 62 of the conduit 56 can be directly applied on top of the soil sample 32 through the opening 46 in the side wall 40 of the vessel 34.

The process illustrated in FIG. 1 shall not be restricted to any particular organic solvent materials in connection with the solvent 52 provided that they are able to solubilize and otherwise dissolve the portions 14 of solid organic explosive material in a partial or complete manner so that such portions 14 are "redistributed" within the soil sample 32. Likewise, in a preferred embodiment, the selected solvent 52 should be (1) substantially biodegradable by all or part of the natural bacteria within the soil sample 32; (2) capable of dissolving the explosive portions 14 directly within the soil sample 32 as noted above, thereby resulting in greater dispersion of the explosive so that it is more bioavailable to the bacteria compared with prior systems; (3) relatively inexpensive and readily available; and (4) sufficiently volatile to rapidly evaporate from the soil sample 32 after dissolution of the solid organic explosive composition therein. Exemplary materials suitable for use as the solvent 52 include but are not limited to acetone, pyridine, n,n-dimethylformamide, dimethylsulfoxide, 1-methyl-2-pyrrolidinone, methyl acetate, benzene, toluene, isobutyl acetate, methanol, ethanol, and mixtures thereof (with acetone being preferred alone or combined with one or more other organic solvents.)

In a representative and preferred embodiment, the solvent 52 will be used in an amount equal to about 0.1–380 ml of total solvent 52 per kilogram of contaminated soil 12 (with the exact amount to be employed within the above-listed range depending on the degree of soil contamination and other factors as determined by routine preliminary testing). This range apples to both a single solvent and a mixture of multiple solvents (which shall all add up to the numbers listed above in the foregoing range), with the soil weight being determined prior to the addition of any other ingredients. However, the claimed process shall again not be restricted to any particular quantities in connection with the solvent 52 which may again be determined in a given situation using preliminary pilot testing involving the specific soil materials and contamination levels under consideration.

Various other components may likewise be added to the soil sample 32 within the treatment vessel 34 (e.g. drum 36). For example, in addition to supplying a selected solvent 52 to the soil sample 32, a preferred embodiment of the process will also involve delivery of at least one organic nutrient composition (shown at reference number 66 in FIG. 1) to the soil sample 32 in the vessel 34. The term "organic nutrient composition" as recited herein (which may also be more specifically characterized as an "organic microorganism nutrient composition") shall encompass carbonaceous materials which may be used by the natural bacteria and other organisms (e.g. protozoa, fungi, and the like) in the soil sample 32 as a suitable energy/nutrition source to form a completed biologically-active compost product. Many different organic nutrient compositions may be employed for this purpose (alone or in mixtures) with the present invention not being restricted to any specific nutrient compounds. Exemplary and non-limiting organic nutrient compositions 66 which can be added to the soil sample 32 as an energy source for the natural explosive-degrading bacteria (and other soil-borne organisms) include but are not limited to animal manure (e.g. cow or chicken droppings), sawdust, alfalfa, potatoes, wood chips, lettuce, sugar beet waste, ground corn cobs, and mixtures thereof. A representative mixture of these materials that is suitable for use herein is discussed in Report No. CETHA-TS-CR-93043 from the U.S. Army Environmental Center—Contract No. DACA31-91-D-0079, Task Order No. 01 (August 1993) which is incorporated herein by reference. A compost product containing this mixture includes the following ingredients (in % by volume): (A) 22.6% sawdust; (B) 22.6% alfalfa; (C) 3.2% chicken manure [dry]; (D) 29.0% cow manure; (E) 12.9% potatoes; and (F) the balance involving the contaminated soil sample 32 and any other materials (e.g. the organic solvent 52) combined therewith. Notwithstanding the example provided above, the claimed method shall not be restricted to any particular amounts of the organic nutrient composition 66 which shall be determined in accordance with preliminary pilot testing involving the specific soil materials being treated. However, in an exemplary and representative embodiment, effective results will be achieved if approximately 4–6 kilograms of the selected organic nutrient composition 66 are employed per kilogram of contaminated soil (e.g. soil sample 32). This range apples to both a single nutrient composition 66 and a mixture of multiple nutrient compositions 66 (which shall all add up to the numbers listed above in the foregoing range), with the soil weight being determined prior to the addition of any other ingredients.

It should also be noted that addition of the organic nutrient composition 66 to the soil sample 32 may be undertaken before or after delivery of the organic solvent 52, with both alternatives being considered equivalent and covered under the claim terminology currently presented herein. The process of FIG. 1 shall not be restricted to any delivery order in connection with the various ingredients added to the soil sample 32 including the solvent 52, the nutrient composition 66, and other materials.

Furthermore, in accordance with the chemical and biological processes involved in the present invention, the addition of one or more organic nutrient compositions shall not always be considered an absolute requirement. The natural bacteria in substantially all soil materials are capable of degrading solid organic explosives in the absence of any added nutrients (although this process may occur at a slow or ineffective rate). The need for nutrient supplementation will ultimately depend on the carbon content of the soil, the explosives being degraded, the type/amount of bacteria in the soil, and other related factors as again determined by routine preliminary testing. For example, "peat"-type soil materials which contain considerable amounts of residual vegetable/animal matter in the form of manure, waste vegetation, and the like (e.g. 50% by weight or more of these materials in combination) may not require the addition of a separate carbonaceous nutrient. However, to ensure effective bioremediation and to avoid the need for preliminary carbon-content testing on the soil materials of interest, it is preferred that at least one organic nutrient composition 66 be added to the soil as a default process step unless otherwise indicated in accordance with preliminary research.

Another optional ingredient which may be supplied to the soil sample 32 before or after addition of the other ingredients listed above (including the organic solvent 52 and the organic nutrient composition 66 [if used]) will involve a supply of "dry ice" 70 (frozen carbon dioxide [$CO_{2(s)}$)]) which is positioned within the vessel 34 via the opening 46 and dispersed on top of the soil sample 32. The dry ice 70 is designed to create an inert atmosphere within the vessel 34. The creation of an inert atmosphere is primarily beneficial for safety purposes. Specifically, the dry ice 70 within the vessel 34 will generate (by sublimation) substantial amounts of gaseous carbon dioxide [$CO_{2(g)}$]. As a result, the carbon dioxide will displace oxygen which is produced in the head-space of the vessel 34 during composting, thereby reducing the possibility of fire and explosion inside the vessel 34. The term "head-space" as used herein involves the open zone above the surface of the soil materials in the vessel 34.

The present invention shall not be restricted regarding the amount of dry ice 70 to be employed (which is optional). In particular, any quantity of dry ice 70 will provide beneficial results, with greater amounts offering increased benefits. However, in general, it is preferred that a sufficient amount of dry ice 70 be used to create an atmosphere within the head-space of the vessel 34 (e.g. drum 36) that is less than about 11% by weight oxygen [$O_{2(g)}$] as determined using conventional oxygen testing equipment taking into consideration the size of the vessel 34, the vessel head-space, and other factors. Specifically, to reach this desired level, dry ice 70 should be added to the interior of the vessel 34 until the oxygen testing system indicates that the desired atmospheric conditions outlined above have been reached. However, the vessel 34 should be monitored to avoid the formation of excessive carbon dioxide pressure within the vessel 34. If needed, periodic releases of carbon dioxide from the vessel 34 should be undertaken to prevent excess pressure generation.

In a representative and preferred embodiment, the treatment vessel 34 will include an optional motor-driven rotation system 72 of conventional design which includes an electric motor 74 that is operatively connected via drive shaft 76 (and other standard connecting hardware) to the first end 42 of the vessel 34 (e.g. drum 36). The system 72 is designed to rotate the vessel 34 having the soil sample 32 and the other listed ingredients therein at, for example, a non-limiting rotational speed of about 10–120 RPM (rotations per minute) after closure of the cover member 50 illustrated in FIG. 1. Rotation may be undertaken in either a clockwise or counter-clockwise fashion with equivalent results, and is designed to thoroughly mix the materials present in the vessel 34. Rotation of the vessel 34 may be undertaken for any given time period, with the mixing time associated with the soil sample 32 and other ingredients not being of a critical nature. However, in an exemplary embodiment, the vessel 34 (and materials therein) will be rotated at the speed listed above for a time period of about 5–10 minutes. The interior region 80 of the vessel 34 may likewise contain one or more optional motor-driven mixing paddles, tines, or vanes (not shown) which can be used to effectively mix the materials inside the vessel 34 in place of the external rotation system 72 discussed above.

At this stage in the production process, the bacteria-containing soil sample 32 combined with the organic solvent 52 and organic nutrient composition 66 (if used) will constitute a mixture designated herein as an "explosive-degrading compost product" 82. Within the compost product 82, the previously-added organic solvent 52 will effectively dissolve the solid organic explosive materials (including the large portions 14 or "chunks", as well as smaller units of explosive material) in order to solubilize these compositions and disperse them within the compost product 82. As a result, the dissolved organic explosive compositions become more bioavailable to the soil-borne bacteria so that the entire bioremediation process is enhanced. Specifically, the dissolution/redistribution process discussed herein allows the bacteria to effectively consume the large portions 14 of explosive material which would not be effectively degraded in conventional bioremediation systems. This is an important distinguishing characteristic of the present invention which is highly beneficial.

The compost product 82 illustrated in FIG. 1 does not include the large portions 14 of explosive material therein which have been dissolved as previously noted. Nonetheless, the compost product 82 does, in fact, have the explosive composition left therein, but in dissolved (e.g. "redistributed") form. Allowing the explosive composition to remain within the compost product 82 is a departure from conventional solvent-extraction and other methods in which the explosive is removed (along with the solvent if appropriate). Dissolution time relative to the large portions 14 of explosive material is usually very rapid and will depend on a variety of factors including the amount of soil sample 32 being treated, the degree of mixing associated with the sample 32 during preparation of the compost product 82, the quantity of solvent 52 added to the system, and other factors. However, it is expected under most circumstances involving the operational parameters discussed above that complete dissolution of the solid explosive composition (including portions 14) will occur over a time period of about 0.5–30 minutes.

At this point, the claimed process includes a very important step which represents a considerable departure from conventional solvent-extraction methods. As stated above, the solvent materials in solvent-extraction processes are simply used to dissolve the explosive materials in the soil, followed by removal of the explosive-laden solvent from the soil for further treatment or disposal (which can represent a difficult, costly, and hazardous problem). In direct contrast, the next step in the present invention involves maintaining the dissolved explosive composition within the compost product 82 (e.g. soil sample 32) for a time period sufficient to enable the natural soil-borne bacteria to chemically break down the explosive composition directly within the soil sample 32/compost product 82. As a result, the explosive materials (including those which were previously present in the form of large portions 14) are eliminated from the compost product 82 in contrast to solvent-extraction or physical treatment systems which require the remaining explosives to be removed and further processed.

While the invention shall not be restricted to any particular time parameters in connection with the "composting" stage and bacterial consumption of the explosive materials, it is a beneficial feature of the claimed process that these goals can be achieved over a time period of not more than about 15 days (about 5–10 days in most situations). The appropriate time period will vary based on multiple factors including the type of explosive being consumed, the level of soil contamination, and other factors. However, this time period is substantially shorter compared with prior composting systems which do not employ a solvent pre-treatment stage and the other unique items listed above. This is particularly true in connection with the bioremediation of soil containing large portions 14 or chunks of organic explosives which are not subject to effective bioremediation using standard composting methods. Effective metabolic consumption of chunk-type explosive materials in the claimed process is accomplished using the novel solvent pre-treatment stage which increases the bioavailability of the explosive compounds to the soil-borne bacteria through the effective dissolution and "redistribution" of such materials.

During the composting process, sufficient heat will be generated to raise the overall temperature of the compost product 82 to about 40–70° C. which enables the entire procedure to be monitored. Likewise, during composting, the organic explosive materials will be biochemically converted to other, non-toxic metabolic products. These products will vary based on numerous factors ranging from the type of explosives being treated to the nutritional content of the soil sample 32. However, in most cases involving the operational parameters set forth herein, the following reaction by-products will be generated by the bacteria during the composting process: 4-amino-2,6-dinitrotoluene; 2-amino-4,6-dinitrotoluene; 2,4-diamino-6-nitrotoluene; and 2,6-diamino-4-nitrotoluene. In accordance with this conversion pathway, the elimination of explosive materials from the soil sample 32 will occur in a highly efficient manner. The claimed invention is capable of eliminating up to about 99% of the explosive materials originally present in the soil sample 32 (including the large portions 14 which would not be effectively consumable in conventional bioremediation systems). In addition to elimination of the explosive materials by the natural bacteria in the soil 12 as discussed above, other soil-borne organisms (including but not limited to protozoa, fungi, and the like) within the compost product 82 will likewise assist in metabolic consumption of the organic explosive compounds, thereby resulting in a highly effective, multi-organism bioremediation system.

Regarding the organic solvent 52, it is ultimately eliminated from the compost product 82 by two pathways. First, it is preferred that the interior region 80 of the containment vessel 34 remain in contact with the surrounding environment (e.g. by leaving the cover member 50 entirely or partially open during the degradation process) which will enable the solvent 52 to effectively evaporate from the system. This evaporative process is facilitated by the chemical volatility of the solvent 52 being employed, as well as the heat generated by the bacteria during the decomposition process. Second, some or all of the natural bacteria in the soil sample 32 which are capable of degrading the explosive materials discussed above are likewise able to degrade and otherwise consume the solvent 52 for use as an energy source. In this manner, both the solvent 52 and explosive materials (e.g. large portions 14) can be totally removed from the system which is a clear departure from prior bioremediation methods.

After completion of the process illustrated in FIG. 1 (in which virtually all of the explosive materials including the large portions 14) are eliminated, the completed decontaminated soil which is shown in FIG. 1 at reference number 84 can be safely returned to the environment. The resulting decontaminated soil 84 is characterized by the absence of residual solvents and/or explosive materials therein. In order to demonstrate the effectiveness of the procedures discussed above compared with conventional composting methods, the following Example is provided.

EXAMPLE

1. Preliminary Information

Two separate bioremediation experiments were conducted involving soil contaminated with solid trinitrotoluene ("TNT"). The soil was obtained from TNT-contaminated areas at the Idaho National Engineering and Environmental Laboratory ("INEEL") located at Idaho Falls, Ind. (USA). The bioremediation procedures discussed above were implemented involving these soil materials with and without the use of a solvent pre-treatment stage. The contaminated soil materials employed in the tests initially contained about 0.004 grams of TNT per gram of test soil (about 0.4% by weight TNT). In addition, the soil contained TNT portions ranging in weight from dust-type microgram/nanogram values to up to about 5.6 grams (which could present effectiveness problems in traditional composting systems). The solvent material used in both tests consisted of acetone employed in an amount equal to about 0.38 ml of acetone/gram of soil (prior to the addition of any organic nutrient compositions or other materials). The specific amount of soil used per test was about 500 grams.

Added to each soil sample was an organic nutrient composition of the type discussed in Report No. CETHA-TS-CR-93043 from the U.S. Army Environmental Center—Contract No. DACA31-91-D-0079, Task Order No. 01 (August 1993) which is incorporated herein by reference. This composition contained sawdust, alfalfa, chicken manure (dry), cow manure, and potatoes. These materials were used in an amount sufficient to form the following mixed product (in % by volume): (A) 22.6% sawdust; (B) 22.6% alfalfa; (C) 3.2% chicken manure [dry]; (D) 29.0% cow manure; (E) 12.9% potatoes; and (F) the balance involving the contaminated soil and any other materials (e.g. acetone) combined therewith.

The test soil samples (with and without acetone) were placed in 350 ml square-bottomed plastic unsealed flasks which were incubated in a 55° C. incubator with daily mixing and moisture (e.g. water) additions to 40–60% of the overall water-holding capacity (when needed). While the basic method described herein does not need any incubation or exposure to increased temperatures, the test samples in this Example were incubated in order to ensure uniformity, consistency, and rapid bacterial digestion. In the test sample involving acetone addition as a solvent pre-treatment, the acetone was added directly to the soil in the appropriate test vessels discussed above, followed by stirring for 30 seconds and hand agitation of the vessels for 30 seconds. For each test (both with and without the addition of acetone), four separate soil samples were involved.

Finally, analytical test data values were obtained through the use of high performance liquid chromatography ("HPLC") tests which were performed using a mixed mode C-18-anion column and a C-18 guard column with a mobile phase of 50% water-50% methanol at a flow rate of 0.64 ml/min. Analytes were also detected with a photodiode array detector at 254 nm. To determine the amount of TNT within the soil samples during the test procedures, soil extractions were undertaken at various time intervals by first drying the soil materials at 50° C., followed by a 2.0 hour acetone sonication, with further information regarding this technique being discussed generally in Jenkins, T. F., "Comparison of Extraction Techniques for Munitions Residues in Soil", *Anal. Chem.*, 59(9):1326–1331 (1987).

2. Test Results

Figure 3:
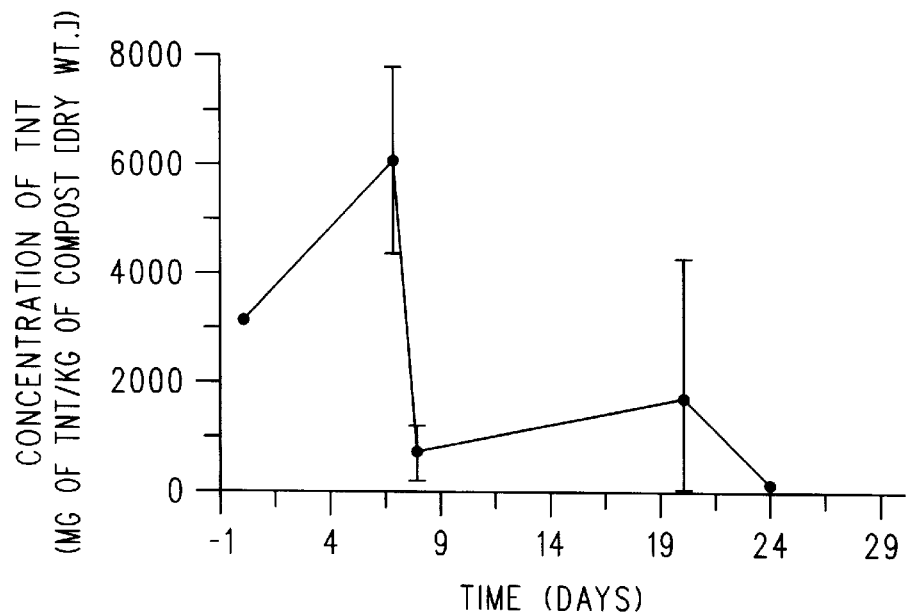
FIG. 3 is a graphical representation of the data received from a soil bioremediation test in which a soil sample containing solid organic explosives was treated using traditional composting methods (excluding the novel solvent pre-treatment stage of the invention).
Figure 4:
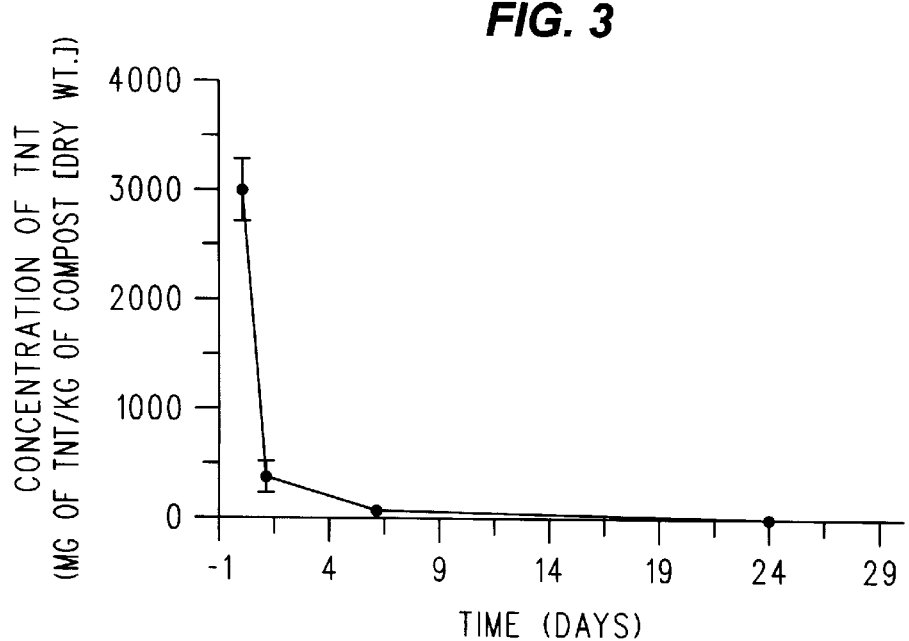
FIG. 4 is a graphical representation of the data received from a soil bioremediation test in which a soil sample containing solid organic explosives was treated using the novel method of the present invention (including the solvent pre-treatment stage which greatly improves the bioavailability of explosive materials).

The test results associated with this Example are graphically shown in FIGS. 3–4. These Figures illustrate the superior bioremediation efficiency associated with the claimed process which involves a unique solvent pre-treatment stage, followed by retention of the dissolved organic explosive materials in the soil for a time period sufficient to biologically consume the explosives. In the graph of FIG. 3 (which did not involve the process of the present invention and lacked any solvent pre-treatment steps), substantial amounts of unremediated (e.g. unconsumed) TNT remained in the soil samples even after twenty (20) days due to bioavailability problems and a lack of overall efficiency. Incidentally, it should noted that the data points in the graph of FIG. 3 fluctuate to form a "jagged" line with alternating higher and lower values since various amounts of small TNT particles were dispersed in a random fashion within the bulk matrix from which samples were taken Also, the "time" scale in the graphs of FIGS. 3–4 begins at "–1" so that the initial starting data points and standard deviation values associated therewith (as characterized by the vertical standard deviation lines discussed below) would be more visible. In any event, FIG. 3 clearly illustrates the prolonged digestion times associated with the TNT-containing test samples due to bioavailability problems.

In direct contrast, the graph of FIG. 4 indicates that substantially all of the TNT in the test samples subjected to solvent pre-treatment was entirely consumed after only about 6–7 days (compared with 20+ days listed above). The superior results of the present invention are clearly demonstrated by a comparison of the information provided by the graphs of FIGS. 3–4, as well as a visual inspection of the graphed data as it applies to both tests.

As a final note, each data point in the graphs of FIGS. 3 and 4 represents test results from four individual soil samples. Accordingly, the data provided for each point constitutes an average value. The vertical lines or "bars" shown in the graphs involve standard deviation values (e.g. one standard deviation up and one standard deviation down). Data points in FIGS. 3 and 4 which do not have these vertical lines associated therewith have standard deviation values which are too small to be seen in the Figures. Data values involving the soil samples associated with FIG. 4 (which underwent the novel solvent pre-treatment process of the claimed invention) showed much less "scatter" from sample to sample compared with the data from the graph of FIG. 3 (in which solvent pre-treatment was not employed). Most of the scatter in both tests was caused by the presence or absence of particulate TNT in the soil samples (some samples contained more TNT in particulate form, while other samples contained more TNT in a solubilized form). The smaller vertical standard deviation lines in the graph of FIG. 4 (involving solvent pre-treatment) indicate that a substantial portion of the TNT in these test samples was solubilized prior to treatment, with the larger vertical bars in the graph of FIG. 3 (which did not involve solvent pre-treatment) indicating that more TNT in particulate form was initially present in these samples. In any event, the data in FIGS. 3–4 is highly significant in that it shows superior TNT removal in the solvent-treated system (versus the untreated system) in terms of both kinetics and confidence, with the treated system offering faster and more certain bioremediation.

In summary, the present invention employs a distinctive, novel, and highly-effective combination of multiple technologies to decontaminate soil containing large portions of solid organic explosive materials therein which are not effectively eliminated using conventional bioremediation systems. The claimed method employs a novel procedure in which solid explosive materials are initially dissolved by a solvent, with the dissolved explosives being allowed to remain in the soil for consumption by soil-borne bacteria. This process clearly departs from prior solvent-extraction methods in which the explosive-laden solvent is removed from the soil for further treatment or disposal. The process of the present invention avoids (A) the generation of explosive-laden hazardous waste products which are generated by standard solvent-extraction methods; and (B) the difficulties associated with composting methods when large portions or "chunks" of explosive materials are treated, namely, the inability of soil bacteria to degrade such materials over a reasonable amount of time (if at all) due to bioavailability problems. The invention offers a number of key benefits including (1) the ability to decontaminate large quantities of organic explosive-containing soil notwithstanding the presence of explosive portions therein of large size that are not normally treatable in an effective manner by traditional bioremediation methods; (2) a considerable improvement in the ability of the soil bacteria to effectively metabolize the desired explosive compounds (regardless of the physical form of such materials); (3) the avoidance of any process steps which generate hazardous waste by-products that require further treatment, disposal, or storage (including contaminated explosive-laden waste solvents); (4) the capability to conduct on-site remediation at a wide variety of geographical locations using a minimal amount of equipment and labor; and (5) the general ability to effectively treat organic explosive-contaminated soil in a manner which is environmentally compatible, rapid, and cost-effective. In accordance with these benefits and the unique combination of process steps described above, the present invention represents an advance in the art of soil decontamination and bioremediation technology.

Having herein described preferred embodiments of the invention, it is anticipated that suitable modifications can be made thereto by individuals skilled in the relevant art which will nonetheless remain within the scope of the invention. For example, the process described above shall not be limited to any particular structures, components, operating parameters, materials, and hardware unless otherwise indicated herein.

We claim:

1. A method for decontaminating soil having a solid organic explosive composition therein comprising:

providing a supply of soil comprising at least one solid organic explosive composition therein, said soil further comprising a supply of natural bacteria within said soil which are able to chemically break down said explosive composition;

delivering at least one organic solvent to said soil which is able to at least partially dissolve said solid organic explosive composition, said solvent coming in contact with said explosive composition and at least partially dissolving said explosive composition in order to make said explosive composition more bioavailable to said bacteria;

delivering at least one organic nutrient composition to said soil; and maintaining said explosive composition in said soil after dissolution thereof for a time period sufficient to enable said bacteria to chemically break down said explosive composition directly within said soil.

2. The method of claim 1 wherein said soil initially comprises about 0.01–10% by weight said solid organic explosive composition therein.

3. The method of claim 1 wherein said delivering of said organic solvent to said soil comprises combining said organic solvent with said soil in an amount equal to about 0.1–380 ml of said organic solvent per kilogram of said soil.

4. The method of claim 1 wherein said solid organic explosive composition is selected from the group consisting of trinitrotoluene, trimethylenetrinitronitramine, tetramethylenetetranitramine, and mixtures thereof.

5. The method of claim 1 wherein said organic solvent is selected from the group consisting of acetone, pyridine, n,n-dimethylformamide, dimethylsulfoxide, 1-methyl-2-pyrrolidinone, methyl acetate, benzene, toluene, isobutyl acetate, methanol, ethanol, and mixtures thereof.

6. The method of claim 1 wherein said time period sufficient to enable said bacteria to chemically break down said explosive composition directly within said soil is about 5–10 days.

7. The method of claim 1 wherein said explosive composition comprises a plurality of individual solid portions thereof each weighing at least about 0.01 grams.

8. A method for decontaminating soil having a solid organic explosive composition therein comprising:

providing a supply of soil comprising about 0.01–10% by weight of at least one solid organic explosive composition therein selected from the group consisting of trinitrotoluene, trimethylenetrinitronitramine, tetramethylenetetranitramine, and mixtures thereof, said explosive composition comprising a plurality of individual solid portions thereof, at least one of said solid portions of said explosive composition weighing at least about 0.01 grams, said soil further comprising a supply of natural bacteria within said soil which are able to chemically break down said explosive composition;

delivering at least one organic solvent to said soil which is able to at least partially dissolve said solid organic explosive composition, said solvent coming in contact with said explosive composition and at least partially dissolving said explosive composition in order to make said explosive composition more bioavailable to said bacteria, said organic solvent being selected from the group consisting of acetone, pyridine, n,n-dimethylformamide, dimethylsulfoxide, 1-methyl-2-pyrrolidinone, methyl acetate, benzene, toluene, isobutyl acetate, methanol, ethanol, and mixtures thereof, said organic solvent being combined with said soil in an amount equal to about 0.1–380 ml of said organic solvent per kilogram of said soil;

delivering at least one organic nutrient composition to said soil; and maintaining said explosive composition in said soil after dissolution thereof for a time period of about 5–10 days in order to enable said bacteria to chemically break down said explosive composition directly within said soil.

9. A method for decontaminating soil having a solid organic explosive composition therein comprising:

providing a supply of soil comprising at least one solid organic explosive composition therein, said soil further comprising a supply of natural bacteria within said soil which are able to chemically break down said explosive composition;

delivering at least one organic solvent to said soil which is able to at least partially dissolve said solid organic explosive composition, said solvent coming in contact with said explosive composition and at least partially dissolving said explosive composition in order to make said explosive composition more bioavailable to said bacteria; and maintaining said explosive composition in said soil after dissolution thereof for a time period sufficient to enable said bacteria to chemically break down said explosive composition directly within said soil.

10. A method for producing a compost product which is used to decontaminate soil having a solid organic explosive composition therein comprising:

providing a supply of soil comprising at least one solid organic explosive composition therein, said soil further comprising a supply of natural bacteria within said soil which are able to chemically break down said explosive composition;

delivering at least one organic solvent to said soil which is able to at least partially dissolve said solid organic explosive composition, said solvent coming in contact with said explosive composition and at least partially dissolving said explosive composition in order to make said explosive composition more bioavailable to said bacteria;

delivering at least one organic nutrient composition to said soil; and leaving said explosive composition in said soil in order to form said compost product.

11. The method of claim 10 wherein said soil initially comprises about 0.01–10% by weight said solid organic explosive composition therein.

12. The method of claim 10 wherein said delivering of said organic solvent to said soil comprises combining said organic solvent with said soil in an amount equal to about 0.1–380 ml of said organic solvent per kilogram of said soil.

13. The method of claim 10 wherein said solid organic explosive composition is selected from the group consisting of trinitrotoluene, trimethylenetrinitronitramine, tetramethylenetetranitramine, and mixtures thereof.

14. The method of claim 10 wherein said organic solvent is selected from the group consisting of acetone, pyridine, n,n-dimethylformamide, dimethylsulfoxide, 1-methyl-2-pyrrolidinone, methyl acetate, benzene, toluene, isobutyl acetate, methanol, ethanol, and mixtures thereof.

15. The product of the method of claim 10.

16. A method for decontaminating soil having a solid organic explosive composition therein comprising:

providing a supply of soil comprising at least one solid organic explosive composition therein, said explosive composition comprising a plurality of individual solid portions of said explosive composition each having a diameter of at least about 5 mm, said soil further comprising a supply of natural bacteria within said soil which are able to chemically break down said explosive composition;

delivering at least one organic solvent to said soil which is able to at least partially dissolve said solid portions of said explosive composition having said diameter, said organic solvent being comprised of acetone, said solvent coming in contact with said solid portions of said explosive composition and at least partially dissolving said solid portions in order to make said solid portions more bioavailable to said bacteria; and maintaining said explosive composition in said soil after dissolution thereof for a time period sufficient to enable said bacteria to chemically break down said explosive composition directly within said soil.

17. A method for decontaminating soil having a solid organic explosive composition therein comprising:

providing a supply of soil comprising at least one solid organic explosive composition therein, said soil further comprising a supply of natural bacteria within said soil which are able to chemically break down said explosive composition;

placing said soil within a treatment vessel;

delivering at least one organic solvent to said soil in said treatment vessel which is able to at least partially dissolve said solid organic explosive composition, said solvent coming in contact with said explosive composition and at least partially dissolving said explosive composition in order to make said explosive composition more bioavailable to said bacteria;

delivering a supply of dry ice into said treatment vessel in order to create an inert atmosphere in said treatment vessel; and maintaining said explosive composition in said soil after dissolution thereof for a time period sufficient to enable said bacteria to chemically break down said explosive composition directly within said soil.

* * * * *